US008109996B2

(12) United States Patent
Stacchino et al.

(10) Patent No.: US 8,109,996 B2

(45) Date of Patent: Feb. 7, 2012

(54) MINIMALLY-INVASIVE CARDIAC-VALVE PROSTHESIS

(75) Inventors: Carla Stacchino, Turin (IT); Giovanni Bergamasco, Turin (IT); Gaetano Burriesci, Palermo (IT)

(73) Assignee: Sorin Biomedica Cardio, S.r.l., Saluggia (Vercelli) (IT)

( * ) Notice: Subject to any disclaimer, the term of this patent is extended or adjusted under 35 U.S.C. 154(b) by 1890 days.

(21) Appl. No.: 11/066,346

(22) Filed: Feb. 25, 2005

(65) Prior Publication Data

US 2005/0197695 A1 Sep. 8, 2005

(30) Foreign Application Priority Data

Mar. 3, 2004 (IT) ............................. TO2004/A0135

(51) Int. Cl.
*A61F 2/24* (2006.01)

(52) U.S. Cl. ...................................... 623/2.17; 623/1.26

(58) Field of Classification Search ................... 623/2.4, 623/2.12, 2.14–2.19

See application file for complete search history.

(56) References Cited

U.S. PATENT DOCUMENTS 3,334,629 A 8/1967 Cohn
3,409,013 A 11/1968 Berry
3,540,431 A 11/1970 Mobin-Uddin
3,587,115 A 6/1971 Shiley
3,608,097 A 9/1971 Bellhouse et al.
3,628,535 A 12/1971 Ostrowsky et al.
3,642,004 A 2/1972 Osthagen et al.
3,657,744 A 4/1972 Ersek
3,671,979 A 6/1972 Moulopoulos
3,744,060 A 7/1973 Bellhouse et al.
3,755,823 A 9/1973 Hancock
3,795,246 A 3/1974 Sturgeon
3,839,741 A 10/1974 Haller
3,868,956 A 3/1975 Alfidi et al.
3,874,388 A 4/1975 King et al.
4,035,849 A 7/1977 Angell et al.
4,056,854 A 11/1977 Boretos et al.
4,086,665 A 5/1978 Poirier
4,106,129 A 8/1978 Carpentier et al.

(Continued)

FOREIGN PATENT DOCUMENTS

DE 3640745 A1 6/1987

(Continued)

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.

(Continued)

*Primary Examiner* — Thomas J Sweet
*Assistant Examiner* — Christopher D Prone
(74) *Attorney, Agent, or Firm* — Faegre & Benson LLP

(57) ABSTRACT

A cardiac-valve prosthesis is adapted for percutaneous implantation. The prosthesis includes an armature adapted for deployment in a radially expanded implantation position, the armature including a support portion and an anchor portion, which are substantially axially coextensive with respect to one another. A set of leaflets is coupled to the support portion. The leaflets can be deployed with the armature in the implantation position. The leaflets define, in the implantation position, a flow duct that is selectably obstructable. The anchor portion can be deployed to enable anchorage of the cardiac-valve prosthesis at an implantation site.

28 Claims, 3 Drawing Sheets

U.S. PATENT DOCUMENTS 4,222,126 A 9/1980 Boretos et al.
4,233,690 A 11/1980 Akins
4,265,694 A 5/1981 Boretos et al.
4,291,420 A 9/1981 Reul
4,297,749 A 11/1981 Davis et al.
4,339,831 A 7/1982 Johnson
4,343,048 A 8/1982 Ross et al.
4,345,340 A 8/1982 Rosen
4,425,908 A 1/1984 Simon
4,451,936 A 6/1984 Carpentier et al.
4,470,157 A 9/1984 Love
4,477,930 A * 10/1984 Totten et al. ................ 623/2.15
4,501,030 A 2/1985 Lane
4,506,394 A 3/1985 Bedard
4,574,803 A 3/1986 Storz
4,580,568 A 4/1986 Gianturco
4,592,340 A 6/1986 Boyles
4,610,688 A 9/1986 Silvestrini et al.
4,612,011 A 9/1986 Kautzky
4,624,822 A 11/1986 Arru et al.
4,647,283 A 3/1987 Carpentier et al.
4,648,881 A 3/1987 Carpentier et al.
4,655,771 A 4/1987 Wallsten
4,662,885 A 5/1987 DiPisa, Jr.
4,665,906 A 5/1987 Jervis
4,681,908 A 7/1987 Broderick et al.
4,692,164 A 9/1987 Dzemeshkevich et al.
4,710,192 A 12/1987 Liotta et al.
4,733,665 A 3/1988 Palmaz
4,758,151 A 7/1988 Arru et al.
4,777,951 A 10/1988 Cribier et al.
4,787,899 A 11/1988 Lazarus
4,796,629 A 1/1989 Grayzel
4,797,901 A 1/1989 Goerne et al.
4,819,751 A 4/1989 Shimada et al.
4,834,755 A 5/1989 Silvestrini et al.
4,856,516 A 8/1989 Hillstead
4,872,874 A 10/1989 Taheri
4,878,495 A 11/1989 Grayzel
4,878,906 A 11/1989 Lindemann et al.
4,883,458 A 11/1989 Shiber
4,909,252 A 3/1990 Goldberger
4,917,102 A 4/1990 Miller et al.
4,922,905 A 5/1990 Strecker
4,954,126 A 9/1990 Wallsten
4,966,604 A 10/1990 Reiss
4,979,939 A 12/1990 Shiber
4,986,830 A 1/1991 Owens et al.
4,994,077 A 2/1991 Dobben
5,002,559 A 3/1991 Tower
5,007,896 A 4/1991 Shiber
5,026,366 A 6/1991 Leckrone
5,032,128 A 7/1991 Alonso
5,037,434 A 8/1991 Lane
5,047,041 A 9/1991 Samuels
5,059,177 A 10/1991 Towne et al.
5,061,273 A 10/1991 Yock
5,084,151 A 1/1992 Vallana et al.
5,085,635 A 2/1992 Cragg
5,089,015 A 2/1992 Ross
5,123,919 A 6/1992 Sauter et al.
5,133,845 A 7/1992 Vallana et al.
5,139,515 A 8/1992 Robicsek
5,152,771 A 10/1992 Sabbaghian et al.
5,161,547 A 11/1992 Tower
5,163,953 A 11/1992 Vince
5,163,954 A 11/1992 Curcio et al.
5,167,628 A 12/1992 Boyles
5,217,483 A 6/1993 Tower
5,232,445 A 8/1993 Bonzel
5,272,909 A 12/1993 Nguyen et al.
5,295,958 A 3/1994 Shturman
5,314,468 A 5/1994 Ramos Martinez
5,327,774 A 7/1994 Nguyen et al.
5,332,402 A 7/1994 Teitelbaum
5,350,398 A 9/1994 Pavcnik et al.
5,370,684 A 12/1994 Vallana et al.
5,370,685 A 12/1994 Stevens
5,387,247 A 2/1995 Vallana et al.
5,389,106 A 2/1995 Tower
5,397,351 A 3/1995 Pavcnik et al.
5,411,552 A 5/1995 Andersen et al.
5,415,633 A 5/1995 Lazarus et al.
5,423,886 A 6/1995 Arru et al.
5,431,676 A 7/1995 Dubrul et al.
5,443,446 A 8/1995 Shturman
5,449,384 A 9/1995 Johnson
5,480,424 A 1/1996 Cox
5,489,294 A 2/1996 McVenes et al.
5,489,297 A 2/1996 Duran
5,496,346 A 3/1996 Horzewski et al.
5,507,767 A 4/1996 Maeda et al.
5,545,209 A 8/1996 Roberts et al.
5,545,211 A 8/1996 An et al.
5,545,214 A 8/1996 Stevens
5,545,215 A 8/1996 Duran
5,554,185 A 9/1996 Block et al.
5,575,818 A 11/1996 Pinchuk
5,580,922 A 12/1996 Park et al.
5,591,195 A 1/1997 Taheri et al.
5,609,626 A 3/1997 Quijano et al.
5,645,559 A 7/1997 Hachtman et al.
5,665,115 A 9/1997 Cragg
5,667,523 A 9/1997 Bynon et al.
5,674,277 A 10/1997 Freitag
5,695,498 A 12/1997 Tower
5,702,368 A 12/1997 Stevens et al.
5,712,953 A 1/1998 Langs
5,713,953 A 2/1998 Vallana et al.
5,716,417 A 2/1998 Girard et al.
5,746,709 A 5/1998 Rom et al.
5,749,890 A 5/1998 Shaknovich
5,766,151 A 6/1998 Valley et al.
5,782,809 A 7/1998 Umeno et al.
5,800,456 A 9/1998 Maeda et al.
5,800,508 A 9/1998 Goicoechea et al.
5,817,126 A 10/1998 Imran
5,824,037 A 10/1998 Fogarty et al.
5,824,041 A 10/1998 Lenker et al.
5,824,043 A 10/1998 Cottone, Jr.
5,824,053 A 10/1998 Khosravi et al.
5,824,056 A 10/1998 Rosenberg
5,824,061 A 10/1998 Quijano et al.
5,824,064 A 10/1998 Taheri
5,840,081 A 11/1998 Andersen et al.
5,843,158 A 12/1998 Lenker et al.
5,843,244 A 12/1998 Pelton et al.
5,851,232 A 12/1998 Lois
5,855,597 A 1/1999 Jayaraman
5,855,601 A 1/1999 Bessler et al.
5,860,996 A 1/1999 Urban et al.
5,861,028 A 1/1999 Angell
5,868,783 A 2/1999 Tower
5,876,436 A 3/1999 Vanney et al.
5,876,448 A 3/1999 Thompson et al.
5,888,201 A 3/1999 Stinson et al.
5,891,191 A 4/1999 Stinson
5,891,195 A 4/1999 Klostermeyer et al.
5,906,619 A 5/1999 Olson et al.
5,907,893 A 6/1999 Zadno-Azizi et al.
5,913,842 A 6/1999 Boyd et al.
5,925,063 A 7/1999 Khosravi
5,944,738 A 8/1999 Amplatz et al.
5,954,766 A 9/1999 Zadno-Azizi et al.
5,957,949 A 9/1999 Leonhardt et al.
5,968,068 A 10/1999 Dehdashtian et al.
5,980,570 A 11/1999 Simpson
5,984,957 A 11/1999 Laptewicz, Jr. et al.
5,997,573 A 12/1999 Quijano et al.
6,022,370 A 2/2000 Tower
6,027,525 A 2/2000 Suh et al.
6,029,671 A 2/2000 Stevens et al.
6,042,589 A 3/2000 Marianne
6,042,598 A 3/2000 Tsugita et al.
6,042,607 A 3/2000 Williamson, IV et al.
6,051,104 A 4/2000 Oriaran et al.
6,059,809 A 5/2000 Amor et al.

6,110,201 A 8/2000 Quijano et al.
6,146,366 A 11/2000 Schachar
6,159,239 A 12/2000 Greenhalgh
6,162,208 A 12/2000 Hipps
6,162,245 A 12/2000 Jayaraman
6,168,614 B1 1/2001 Andersen et al.
6,171,335 B1 1/2001 Wheatley et al.
6,197,143 B1 3/2001 Bodnar
6,200,336 B1 3/2001 Pavcnik et al.
6,203,550 B1 3/2001 Olson
6,210,408 B1 4/2001 Chandrasekaran et al.
6,218,662 B1 4/2001 Tchakarov et al.
6,221,006 B1 4/2001 Dubrul et al.
6,221,091 B1 4/2001 Khosravi
6,241,757 B1 6/2001 An et al.
6,245,102 B1 6/2001 Jayaraman
6,248,116 B1 6/2001 Chevillon et al.
6,258,114 B1 7/2001 Konya et al.
6,258,115 B1 7/2001 Dubrul
6,258,120 B1 7/2001 McKenzie et al.
6,270,526 B1 8/2001 Cox
6,277,555 B1 8/2001 Duran et al.
6,299,637 B1 10/2001 Shaolian et al.
6,299,638 B1 10/2001 Sauter
6,302,906 B1 10/2001 Goicoechea et al.
6,309,382 B1 10/2001 Garrison et al.
6,309,417 B1 10/2001 Spence et al.
6,312,462 B1 11/2001 McDermott et al.
6,338,735 B1 1/2002 Stevens
6,348,063 B1 2/2002 Yassour et al.
6,350,277 B1 2/2002 Kocur
6,352,554 B2 3/2002 De Paulis
6,352,708 B1 3/2002 Duran et al.
6,371,970 B1 4/2002 Khosravi et al.
6,371,983 B1 4/2002 Lane
6,379,383 B1 4/2002 Palmaz et al.
6,380,457 B1 4/2002 Yurek et al.
6,398,807 B1 6/2002 Chouinard et al.
6,402,780 B2 6/2002 Williamson, IV et al.
6,409,750 B1 6/2002 Hyodoh et al.
6,424,885 B1 7/2002 Niemeyer et al.
6,425,916 B1 * 7/2002 Garrison et al. ............ 623/2.11
6,440,164 B1 8/2002 DiMatteo et al.
6,454,799 B1 9/2002 Schreck
6,458,153 B1 10/2002 Bailey et al.
6,461,382 B1 10/2002 Cao
6,468,303 B1 10/2002 Amplatz et al.
6,475,239 B1 11/2002 Campbell et al.
6,482,228 B1 11/2002 Norred
6,488,704 B1 12/2002 Connelly et al.
6,493,608 B1 12/2002 Niemeyer
6,494,909 B2 12/2002 Greenhalgh
6,503,272 B2 1/2003 Duerig et al.
6,508,833 B2 1/2003 Pavcnik et al.
6,527,800 B1 3/2003 McGuckin, Jr. et al.
6,530,949 B2 3/2003 Konya et al.
6,544,285 B1 4/2003 Thubrikar et al.
6,562,031 B2 5/2003 Chandrasekaran et al.
6,562,058 B2 5/2003 Seguin et al.
6,569,196 B1 5/2003 Vesely
6,582,462 B1 6/2003 Andersen et al.
6,585,758 B1 7/2003 Chouinard et al.
6,592,546 B1 7/2003 Barbut et al.
6,605,112 B1 8/2003 Moll et al.
6,613,077 B2 9/2003 Gilligan et al.
6,622,604 B1 9/2003 Chouinard et al.
6,635,068 B1 10/2003 Dubrul et al.
6,652,571 B1 11/2003 White et al.
6,652,578 B2 11/2003 Bailey et al.
6,656,213 B2 12/2003 Solem
6,656,219 B1 12/2003 Wiktor
6,663,663 B2 12/2003 Kim et al.
6,669,724 B2 12/2003 Park et al.
6,673,089 B1 1/2004 Yassour et al.
6,673,109 B2 1/2004 Cox
6,676,684 B1 1/2004 Morley et al.
6,676,698 B2 1/2004 McGuckin, Jr. et al.
6,682,558 B2 1/2004 Tu et al.
6,685,739 B2 2/2004 DiMatteo et al.
6,689,144 B2 2/2004 Gerberding
6,689,164 B1 2/2004 Seguin
6,692,512 B2 2/2004 Jang
6,692,513 B2 2/2004 Streeter et al.
6,695,878 B2 2/2004 McGuckin, Jr. et al.
6,702,851 B1 3/2004 Chinn et al.
6,719,789 B2 4/2004 Cox
6,730,118 B2 5/2004 Spenser et al.
6,730,377 B2 5/2004 Wang
6,733,525 B2 5/2004 Yang et al.
6,736,846 B2 5/2004 Cox
6,752,828 B2 6/2004 Thornton
6,758,855 B2 7/2004 Fulton, III et al.
6,769,434 B2 8/2004 Liddicoat et al.
6,786,925 B1 9/2004 Schoon et al.
6,790,229 B1 9/2004 Berreklouw
6,790,230 B2 9/2004 Beyersdorf et al.
6,792,979 B2 9/2004 Konya et al.
6,797,002 B2 9/2004 Spence et al.
6,805,711 B2 10/2004 Quijano et al.
6,821,297 B2 11/2004 Snyders
6,830,575 B2 12/2004 Stenzel et al.
6,830,584 B1 12/2004 Seguin
6,830,585 B1 12/2004 Artof et al.
6,846,325 B2 1/2005 Liddicoat
6,866,650 B2 3/2005 Stevens et al.
6,872,223 B2 3/2005 Roberts et al.
6,875,231 B2 4/2005 Anduiza et al.
6,883,522 B2 4/2005 Spence et al.
6,887,266 B2 5/2005 Williams et al.
6,890,330 B2 5/2005 Streeter et al.
6,893,460 B2 5/2005 Spenser et al.
6,896,690 B1 5/2005 Lambrecht et al.
6,908,481 B2 6/2005 Cribier
6,913,600 B2 7/2005 Valley et al.
6,929,653 B2 8/2005 Strecter
6,936,066 B2 8/2005 Palmaz et al.
6,939,365 B1 9/2005 Fogarty et al.
6,974,474 B2 12/2005 Pavcnik et al.
6,974,476 B2 12/2005 McGuckin, Jr. et al.
6,986,742 B2 1/2006 Hart et al.
6,989,027 B2 1/2006 Allen et al.
6,989,028 B2 1/2006 Lashinski et al.
6,991,649 B2 1/2006 Sievers
7,018,401 B1 3/2006 Hyodoh et al.
7,018,404 B2 3/2006 Holmberg et al.
7,041,128 B2 5/2006 McGuckin, Jr. et al.
7,044,966 B2 5/2006 Svanidze et al.
7,048,014 B2 5/2006 Hyodoh et al.
7,097,659 B2 8/2006 Woolfson et al.
7,105,016 B2 9/2006 Shiu et al.
7,115,141 B2 10/2006 Menz et al.
7,125,418 B2 10/2006 Duran et al.
7,128,759 B2 10/2006 Osborne et al.
7,147,663 B1 12/2006 Berg et al.
7,153,324 B2 12/2006 Case et al.
7,160,319 B2 1/2007 Chouinard et al.
7,175,656 B2 2/2007 Khairkhahan
7,186,265 B2 3/2007 Sharkawy et al.
7,195,641 B2 3/2007 Palmaz et al.
7,198,646 B2 4/2007 Figulla et al.
7,201,761 B2 4/2007 Woolfson et al.
7,201,772 B2 4/2007 Schwammenthal et al.
7,211,107 B2 5/2007 Bruckheimer
7,252,682 B2 8/2007 Seguin
7,255,706 B2 8/2007 Rosengart
7,261,732 B2 8/2007 Justino
7,300,457 B2 11/2007 Palmaz
7,300,463 B2 11/2007 Liddicoat
7,316,706 B2 1/2008 Bloom et al.
7,329,278 B2 2/2008 Seguin et al.
7,329,279 B2 2/2008 Haug et al.
7,335,218 B2 2/2008 Wilson et al.
7,338,520 B2 3/2008 Bailey et al.
7,347,869 B2 3/2008 Hojeibane et al.
7,351,256 B2 4/2008 Hojeibane et al.
7,374,571 B2 5/2008 Pease et al.
7,377,938 B2 5/2008 Sarac et al.
7,381,218 B2 6/2008 Schreck

| | | | |
|---|---|---|---|
| 7,384,411 | B1 | 6/2008 | Condado |
| 7,393,360 | B2 | 7/2008 | Spenser et al. |
| 7,429,269 | B2 | 9/2008 | Schwammenthal et al. |
| 7,442,204 | B2 | 10/2008 | Schwammenthal et al. |
| 7,462,191 | B2 | 12/2008 | Spenser et al. |
| 7,470,284 | B2 | 12/2008 | Lambrecht et al. |
| 7,481,838 | B2 | 1/2009 | Carpentier et al. |
| 7,544,206 | B2 | 6/2009 | Cohn |
| 7,547,322 | B2 | 6/2009 | Sarac et al. |
| 7,556,646 | B2 | 7/2009 | Yang et al. |
| 7,578,843 | B2 | 8/2009 | Shu |
| 7,585,321 | B2 | 9/2009 | Cribier |
| 7,591,848 | B2 | 9/2009 | Allen |
| 7,618,446 | B2 | 11/2009 | Andersen et al. |
| 7,618,447 | B2 | 11/2009 | Case et al. |
| 7,682,390 | B2 | 3/2010 | Seguin |
| 7,780,726 | B2 | 8/2010 | Seguin |
| 7,857,845 | B2 | 12/2010 | Stacchino et al. |
| 2001/0001314 | A1 | 5/2001 | Davison et al. |
| 2001/0002445 | A1 | 5/2001 | Vesely |
| 2001/0007956 | A1 | 7/2001 | Letac et al. |
| 2001/0010017 | A1 | 7/2001 | Letac et al. |
| 2001/0011189 | A1 | 8/2001 | Drasler et al. |
| 2001/0021872 | A1 | 9/2001 | Bailey et al. |
| 2001/0025196 | A1 | 9/2001 | Chinn et al. |
| 2001/0032013 | A1 | 10/2001 | Marton |
| 2001/0039450 | A1 | 11/2001 | Pavcnik et al. |
| 2001/0041928 | A1 | 11/2001 | Pavcnik et al. |
| 2001/0044647 | A1 | 11/2001 | Pinchuk et al. |
| 2002/0010508 | A1 | 1/2002 | Chobotov |
| 2002/0029014 | A1 | 3/2002 | Jayaraman |
| 2002/0032480 | A1 | 3/2002 | Spence et al. |
| 2002/0032481 | A1 | 3/2002 | Gabbay |
| 2002/0035396 | A1 | 3/2002 | Heath |
| 2002/0042650 | A1 | 4/2002 | Vardi et al. |
| 2002/0042651 | A1 | 4/2002 | Liddicoat et al. |
| 2002/0058995 | A1 | 5/2002 | Stevens |
| 2002/0072789 | A1 | 6/2002 | Hackett et al. |
| 2002/0095209 | A1 | 7/2002 | Zadno-Azizi et al. |
| 2002/0103533 | A1 | 8/2002 | Langberg et al. |
| 2002/0107565 | A1 | 8/2002 | Greenhalgh |
| 2002/0111674 | A1 | 8/2002 | Chouinard et al. |
| 2002/0123802 | A1 | 9/2002 | Snyders |
| 2002/0128702 | A1 | 9/2002 | Menz et al. |
| 2002/0133183 | A1 | 9/2002 | Lentz et al. |
| 2002/0133226 | A1 | 9/2002 | Marquez et al. |
| 2002/0138138 | A1 | 9/2002 | Yang |
| 2002/0151970 | A1 | 10/2002 | Garrison et al. |
| 2002/0161392 | A1 | 10/2002 | Dubrul |
| 2002/0161394 | A1 | 10/2002 | Macoviak et al. |
| 2002/0193871 | A1 | 12/2002 | Beyersdorf et al. |
| 2002/0198594 | A1 | 12/2002 | Schreck |
| 2003/0014104 | A1 | 1/2003 | Cribier |
| 2003/0023300 | A1 | 1/2003 | Bailey et al. |
| 2003/0023303 | A1 | 1/2003 | Palmaz et al. |
| 2003/0028247 | A1 | 2/2003 | Cali |
| 2003/0036791 | A1 | 2/2003 | Philipp et al. |
| 2003/0036795 | A1 | 2/2003 | Andersen et al. |
| 2003/0040771 | A1 | 2/2003 | Hyodoh et al. |
| 2003/0040772 | A1 | 2/2003 | Hyodoh et al. |
| 2003/0050694 | A1 | 3/2003 | Yang et al. |
| 2003/0055495 | A1 | 3/2003 | Pease et al. |
| 2003/0065386 | A1 | 4/2003 | Weadock |
| 2003/0069492 | A1 | 4/2003 | Abrams et al. |
| 2003/0109924 | A1 | 6/2003 | Cribier |
| 2003/0125795 | A1 | 7/2003 | Pavcnik et al. |
| 2003/0130726 | A1 | 7/2003 | Thorpe et al. |
| 2003/0130729 | A1 | 7/2003 | Paniagua et al. |
| 2003/0139804 | A1 | 7/2003 | Hankh et al. |
| 2003/0149475 | A1 | 8/2003 | Hyodoh et al. |
| 2003/0149476 | A1 | 8/2003 | Damm et al. |
| 2003/0149478 | A1 | 8/2003 | Figulla et al. |
| 2003/0153974 | A1 | 8/2003 | Spenser et al. |
| 2003/0163194 | A1 | 8/2003 | Quijano et al. |
| 2003/0181850 | A1 | 9/2003 | Diamond et al. |
| 2003/0191519 | A1 | 10/2003 | Lombardi et al. |
| 2003/0191528 | A1 | 10/2003 | Quijano et al. |
| 2003/0199913 | A1 | 10/2003 | Dubrul et al. |
| 2003/0199963 | A1 | 10/2003 | Tower et al. |
| 2003/0208261 | A1 | 11/2003 | Thorpe et al. |
| 2003/0212410 | A1 | 11/2003 | Stenzel et al. |
| 2003/0212454 | A1 | 11/2003 | Scott et al. |
| 2003/0225445 | A1 | 12/2003 | Derus et al. |
| 2004/0019374 | A1 | 1/2004 | Hojeibane et al. |
| 2004/0034407 | A1 | 2/2004 | Sherry |
| 2004/0034411 | A1 | 2/2004 | Quijano et al. |
| 2004/0039436 | A1 | 2/2004 | Spenser et al. |
| 2004/0049224 | A1 | 3/2004 | Buehlmann et al. |
| 2004/0049262 | A1 | 3/2004 | Obermiller et al. |
| 2004/0049266 | A1 | 3/2004 | Anduiza et al. |
| 2004/0055606 | A1 | 3/2004 | Hendricksen et al. |
| 2004/0078072 | A1 | 4/2004 | Tu et al. |
| 2004/0078074 | A1 | 4/2004 | Anderson et al. |
| 2004/0082904 | A1 | 4/2004 | Houde et al. |
| 2004/0088045 | A1 | 5/2004 | Cox |
| 2004/0092858 | A1 | 5/2004 | Wilson et al. |
| 2004/0092989 | A1 | 5/2004 | Wilson et al. |
| 2004/0093005 | A1 | 5/2004 | Durcan |
| 2004/0093060 | A1 | 5/2004 | Seguin et al. |
| 2004/0093070 | A1 | 5/2004 | Hojeibane et al. |
| 2004/0093075 | A1 | 5/2004 | Kuehne |
| 2004/0097788 | A1 | 5/2004 | Mourlas et al. |
| 2004/0098112 | A1 | 5/2004 | DiMatteo et al. |
| 2004/0106976 | A1 | 6/2004 | Bailey et al. |
| 2004/0106990 | A1 | 6/2004 | Spence et al. |
| 2004/0111096 | A1 | 6/2004 | Tu et al. |
| 2004/0116951 | A1 | 6/2004 | Rosengart |
| 2004/0117004 | A1 | 6/2004 | Osborne et al. |
| 2004/0122468 | A1 | 6/2004 | Yodfat et al. |
| 2004/0122514 | A1 | 6/2004 | Fogarty et al. |
| 2004/0122516 | A1 | 6/2004 | Fogarty et al. |
| 2004/0127979 | A1 | 7/2004 | Wilson et al. |
| 2004/0138742 | A1 | 7/2004 | Myers et al. |
| 2004/0138743 | A1 | 7/2004 | Myers et al. |
| 2004/0153146 | A1 | 8/2004 | Lashinski et al. |
| 2004/0167573 | A1 | 8/2004 | Williamson et al. |
| 2004/0167620 | A1 | 8/2004 | Ortiz et al. |
| 2004/0186558 | A1 | 9/2004 | Pavcnik et al. |
| 2004/0186563 | A1 | 9/2004 | Lobbi |
| 2004/0193261 | A1 | 9/2004 | Berreklouw |
| 2004/0210240 | A1 | 10/2004 | Saint |
| 2004/0210304 | A1 | 10/2004 | Seguin et al. |
| 2004/0210307 | A1 | 10/2004 | Khairkhahan |
| 2004/0215333 | A1 | 10/2004 | Duran et al. |
| 2004/0215339 | A1 | 10/2004 | Drasler et al. |
| 2004/0225353 | A1 | 11/2004 | McGuckin et al. |
| 2004/0225354 | A1 | 11/2004 | Allen et al. |
| 2004/0254636 | A1 | 12/2004 | Flagle et al. |
| 2004/0260389 | A1 | 12/2004 | Case et al. |
| 2004/0260394 | A1 | 12/2004 | Douk et al. |
| 2004/0267357 | A1 | 12/2004 | Allen et al. |
| 2005/0010246 | A1 | 1/2005 | Streeter et al. |
| 2005/0010285 | A1 | 1/2005 | Lambrecht et al. |
| 2005/0010287 | A1 | 1/2005 | Macoviak et al. |
| 2005/0015112 | A1 | 1/2005 | Cohn et al. |
| 2005/0027348 | A1 | 2/2005 | Case et al. |
| 2005/0033398 | A1 | 2/2005 | Seguin |
| 2005/0043790 | A1 | 2/2005 | Seguin |
| 2005/0049692 | A1 | 3/2005 | Numamoto et al. |
| 2005/0049696 | A1 | 3/2005 | Siess et al. |
| 2005/0055088 | A1 | 3/2005 | Liddicoat et al. |
| 2005/0060029 | A1 | 3/2005 | Le et al. |
| 2005/0060030 | A1 | 3/2005 | Lashinski et al. |
| 2005/0075584 | A1 | 4/2005 | Cali |
| 2005/0075712 | A1 | 4/2005 | Biancucci et al. |
| 2005/0075713 | A1 | 4/2005 | Biancucci et al. |
| 2005/0075717 | A1 | 4/2005 | Nguyen et al. |
| 2005/0075718 | A1 | 4/2005 | Nguyen et al. |
| 2005/0075719 | A1 | 4/2005 | Bergheim |
| 2005/0075720 | A1 | 4/2005 | Nguyen et al. |
| 2005/0075724 | A1 | 4/2005 | Svanidze et al. |
| 2005/0075726 | A1 | 4/2005 | Svanidze et al. |
| 2005/0075727 | A1 | 4/2005 | Wheatley |
| 2005/0075728 | A1 | 4/2005 | Nguyen et al. |
| 2005/0075729 | A1 | 4/2005 | Nguyen et al. |
| 2005/0075730 | A1 | 4/2005 | Myers et al. |
| 2005/0075731 | A1 | 4/2005 | Artof et al. |
| 2005/0085841 | A1 | 4/2005 | Eversull et al. |

| | | | |
|---|---|---|---|
| 2005/0085842 | A1 | 4/2005 | Eversull et al. |
| 2005/0085843 | A1 | 4/2005 | Opolski et al. |
| 2005/0085890 | A1 | 4/2005 | Rasmussen et al. |
| 2005/0085900 | A1 | 4/2005 | Case et al. |
| 2005/0096568 | A1 | 5/2005 | Kato |
| 2005/0096692 | A1 | 5/2005 | Linder et al. |
| 2005/0096724 | A1 | 5/2005 | Stenzel et al. |
| 2005/0096734 | A1 | 5/2005 | Majercak et al. |
| 2005/0096735 | A1 | 5/2005 | Hojeibane et al. |
| 2005/0096736 | A1 | 5/2005 | Osse et al. |
| 2005/0107871 | A1 | 5/2005 | Realyvasquez et al. |
| 2005/0113910 | A1 | 5/2005 | Paniagua et al. |
| 2005/0119688 | A1 | 6/2005 | Bergheim |
| 2005/0131438 | A1 | 6/2005 | Cohn |
| 2005/0137686 | A1 | 6/2005 | Salahieh et al. |
| 2005/0137687 | A1 | 6/2005 | Salahieh et al. |
| 2005/0137688 | A1 | 6/2005 | Salahieh et al. |
| 2005/0137689 | A1 | 6/2005 | Salahieh et al. |
| 2005/0137690 | A1 | 6/2005 | Salahieh et al. |
| 2005/0137691 | A1 | 6/2005 | Salahieh et al. |
| 2005/0137692 | A1 | 6/2005 | Salahieh et al. |
| 2005/0137693 | A1 | 6/2005 | Salahieh et al. |
| 2005/0137694 | A1 | 6/2005 | Salahieh et al. |
| 2005/0137695 | A1 | 6/2005 | Salahieh et al. |
| 2005/0137696 | A1 | 6/2005 | Salahieh et al. |
| 2005/0137697 | A1 | 6/2005 | Salahieh et al. |
| 2005/0137698 | A1 | 6/2005 | Salahieh et al. |
| 2005/0137699 | A1 | 6/2005 | Salahieh et al. |
| 2005/0137701 | A1 | 6/2005 | Salahieh et al. |
| 2005/0137702 | A1 | 6/2005 | Haug et al. |
| 2005/0143807 | A1 | 6/2005 | Pavcnik et al. |
| 2005/0143809 | A1 | 6/2005 | Salahieh et al. |
| 2005/0148997 | A1 | 7/2005 | Valley et al. |
| 2005/0149181 | A1 | 7/2005 | Eberhardt |
| 2005/0165477 | A1 | 7/2005 | Anduiza et al. |
| 2005/0187616 | A1 | 8/2005 | Realyvasquez |
| 2005/0197695 | A1 | 9/2005 | Stacchino et al. |
| 2005/0203549 | A1 | 9/2005 | Realyvasquez |
| 2005/0203605 | A1 | 9/2005 | Dolan |
| 2005/0203618 | A1 | 9/2005 | Sharkawy et al. |
| 2005/0222674 | A1 | 10/2005 | Paine |
| 2005/0228495 | A1 | 10/2005 | Macoviak |
| 2005/0234546 | A1 | 10/2005 | Nugent et al. |
| 2005/0240263 | A1 | 10/2005 | Fogarty et al. |
| 2005/0261759 | A1 | 11/2005 | Lambrecht et al. |
| 2005/0283962 | A1 | 12/2005 | Boudjemline |
| 2006/0009841 | A1 | 1/2006 | McGuckin et al. |
| 2006/0058775 | A1 | 3/2006 | Stevens et al. |
| 2006/0100685 | A1 | 5/2006 | Seguin et al. |
| 2006/0116757 | A1 | 6/2006 | Lashinski et al. |
| 2006/0135964 | A1 | 6/2006 | Vesely |
| 2006/0142848 | A1 | 6/2006 | Gabbay |
| 2006/0167474 | A1 | 7/2006 | Bloom et al. |
| 2006/0206192 | A1 | 9/2006 | Tower et al. |
| 2006/0247763 | A1 | 11/2006 | Slater |
| 2006/0259134 | A1 | 11/2006 | Schwammenthal et al. |
| 2006/0259137 | A1 | 11/2006 | Artof et al. |
| 2006/0271175 | A1 | 11/2006 | Woolfson et al. |
| 2006/0282161 | A1 | 12/2006 | Huynh et al. |
| 2007/0005129 | A1 | 1/2007 | Damm et al. |
| 2007/0010878 | A1 | 1/2007 | Rafiee et al. |
| 2007/0016286 | A1 | 1/2007 | Herrmann et al. |
| 2007/0027518 | A1 | 2/2007 | Case et al. |
| 2007/0032850 | A1 | 2/2007 | Ruiz et al. |
| 2007/0043435 | A1 | 2/2007 | Seguin et al. |
| 2007/0051377 | A1 | 3/2007 | Douk et al. |
| 2007/0078509 | A1 | 4/2007 | Lotfy |
| 2007/0093869 | A1 | 4/2007 | Bloom et al. |
| 2007/0100435 | A1 | 5/2007 | Case et al. |
| 2007/0106372 | A1 | 5/2007 | Osborne et al. |
| 2007/0112415 | A1 | 5/2007 | Bartlett |
| 2007/0118209 | A1 | 5/2007 | Strecker |
| 2007/0162113 | A1 | 7/2007 | Sharkawy et al. |
| 2007/0168024 | A1 | 7/2007 | Khairkhahan |
| 2007/0185513 | A1 | 8/2007 | Woolfson et al. |
| 2007/0255396 | A1 | 11/2007 | Douk et al. |
| 2008/0009940 | A1 | 1/2008 | Cribier |
| 2008/0021552 | A1 | 1/2008 | Gabbay |
| 2008/0065204 | A1 | 3/2008 | Macoviak et al. |
| 2008/0065206 | A1 | 3/2008 | Liddicoat |
| 2008/0125859 | A1 | 5/2008 | Salahieh et al. |
| 2008/0147105 | A1 | 6/2008 | Wilson et al. |
| 2008/0154356 | A1 | 6/2008 | Obermiller et al. |
| 2008/0215143 | A1 | 9/2008 | Seguin |
| 2008/0255662 | A1 | 10/2008 | Stacchino et al. |
| 2008/0269878 | A1 | 10/2008 | Iobbi |
| 2009/0082858 | A1 | 3/2009 | Nugent et al. |
| 2009/0085900 | A1 | 4/2009 | Weiner |
| 2009/0164004 | A1 | 6/2009 | Cohn |
| 2009/0164006 | A1 | 6/2009 | Seguin et al. |
| 2009/0222082 | A1 | 9/2009 | Lock et al. |
| 2010/0004740 | A1 | 1/2010 | Seguin et al. |
| 2010/0036485 | A1 | 2/2010 | Seguin |
| 2010/0152840 | A1 | 6/2010 | Seguin et al. |
| 2010/0198346 | A1 | 8/2010 | Keogh et al. |

FOREIGN PATENT DOCUMENTS

| | | | |
|---|---|---|---|
| DE | 19532846 | A1 | 3/1997 |
| DE | 195 46 692 | C2 | 6/1997 |
| DE | 198 57 887 | A1 | 7/2000 |
| DE | 19907646 | A1 | 8/2000 |
| DE | 10010074 | A1 | 10/2001 |
| DE | 10049812 | A1 | 4/2002 |
| DE | 10049813 | C1 | 4/2002 |
| DE | 10049815 | A1 | 4/2002 |
| DE | 10121210 | A1 | 11/2002 |
| DE | 10301026 | A1 | 2/2004 |
| EP | 0 133 420 | B1 | 2/1988 |
| EP | 0155245 | B1 | 5/1990 |
| EP | 0 592 410 | B1 | 10/1995 |
| EP | 0515324 | B1 | 12/1996 |
| EP | 0 850 607 | A1 | 7/1998 |
| EP | 1 057 460 | A1 | 12/2000 |
| EP | 1 088 529 | A2 | 4/2001 |
| EP | 1259194 | B1 | 2/2005 |
| EP | 1214020 | B1 | 3/2005 |
| EP | 1014896 | B1 | 11/2005 |
| EP | 1469797 | A1 | 11/2005 |
| EP | 1603493 | A2 | 12/2005 |
| EP | 1600127 | B1 | 11/2006 |
| EP | 1255510 | A1 | 4/2007 |
| EP | 1143882 | B1 | 12/2007 |
| EP | 1570809 | B1 | 1/2009 |
| EP | 1330213 | B1 | 3/2009 |
| EP | 2055266 | A2 | 5/2009 |
| EP | 1370201 | B1 | 9/2009 |
| EP | 2133039 | A2 | 12/2009 |
| FR | 2788217 | A1 | 7/2000 |
| FR | 2815844 | A1 | 1/2003 |
| GB | 2056023 | A | 8/1983 |
| NL | 1017275 | C2 | 8/2002 |
| SU | 1271508 | A1 | 11/1986 |
| WO | WO9529640 | A1 | 11/1995 |
| WO | WO 97/24989 | | 7/1997 |
| WO | WO 98/17202 | | 4/1998 |
| WO | WO 98/29057 | | 7/1998 |
| WO | WO9913802 | A1 | 3/1999 |
| WO | WO 99/56665 | | 11/1999 |
| WO | WO 00/41652 | | 7/2000 |
| WO | WO0044313 | A1 | 8/2000 |
| WO | WO0047136 | A1 | 8/2000 |
| WO | WO0047139 | A1 | 8/2000 |
| WO | WO0062714 | A1 | 10/2000 |
| WO | WO0062716 | A1 | 10/2000 |
| WO | WO0121107 | A1 | 3/2001 |
| WO | WO0135870 | A1 | 5/2001 |
| WO | WO0149213 | A2 | 7/2001 |
| WO | WO 01/62189 | A1 | 8/2001 |
| WO | WO0154625 | A1 | 8/2001 |
| WO | WO 01/64137 | A1 | 9/2001 |
| WO | WO 01/76510 | A2 | 10/2001 |
| WO | WO0222054 | A1 | 3/2002 |
| WO | WO 02/41789 | A2 | 5/2002 |
| WO | WO0236048 | A1 | 5/2002 |
| WO | WO 02/47575 | A2 | 6/2002 |
| WO | WO 02/076348 | A1 | 10/2002 |
| WO | WO 03/003943 | A2 | 1/2003 |
| WO | WO03011195 | A2 | 2/2003 |

| | | | |
|---|---|---|---|
| WO | WO 03/094797 | A1 | 11/2003 |
| WO | WO03003949 | A2 | 1/2004 |
| WO | WO2004019825 | A1 | 3/2004 |
| WO | WO2004082527 | A2 | 9/2004 |
| WO | WO2004089250 | A1 | 10/2004 |
| WO | WO2005004753 | A1 | 1/2005 |
| WO | WO2004091455 | A2 | 2/2005 |
| WO | WO2005046528 | A1 | 5/2005 |

OTHER PUBLICATIONS

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

Bailey, "Percutaneous Expandable Prosthetic Valves," In: Topol EJ, ed. Textbook of Interventional Cardiology. vol. II. Second edition. WB Saunders, Philadelphia, 1994:1268-1276.

Block, et al., "Percutaneous Approaches to Valvular Heart Disease," Current Cardiology Reports, vol. 7 (2005) pp. 108-113.

Bonhoeffer, et al, "Percutaneous Insertion of the Pulmonary Valve," Journal of the American College of Cardiology (United States), May 15, 2002, pp. I 664-669.

Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.

Bonhoeffer, et al, "Transcatheter Implantation of a Bovine Valve in Pulmonary Position: A Lamb Study," Circulation (United States), Aug. 15, 2000, pp. 813-816.

Boudjemline, et al, "Images in Cardiovascular Medicine. Percutaneous Aortic Valve Replacement in Animals," Circulation (United States), Mar. 16, 2004.

Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.

Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.

Boudjemline, et al, "Percutaneous Aortic Valve Replacement: Will We Get There?" Heart (British Cardiac Society) (England), Dec. 2001, pp. 705-706.

Boudjemline, et al, "Percutaneous Implantation of a Biological Valve in Aortic Position: Preliminary Results in a Sheep Study," European Heart Journal 22, Sep. 2001, p. 630.

Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.

Boudjemline, et al, "Percutaneous Implantation of a Valve in the Descending Aorta in Lambs," European Heart Journal (England), Jul. 2002, pp. 1045-1049.

Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.

Boudjemline, et al, "Percutaneous Valve Insertion: A New Approach," Journal of Thoracic and Cardiovascular Surgery (United States), Mar. 2003, pp. 741-742.

Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.

Boudjemline, et al, "Steps Toward Percutaneous Aortic Valve Replacement," Circulation (United States), Feb. 12, 2002, pp. 775-778.

Boudjemline, et al, "The Percutaneous Implantable Heart Valve," Progress in Pediatric Cardiology (Ireland), 2001, pp. 89-93.

Boudjemline, et al, "Transcatheter Reconstruction of the Right Heart," Cardiology in the Young (England), Jun. 2003, pp. 308-311.

Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.

Cribier, A. et al, "Percutaneous Transcatheter Implantation of an Aortic Valve Prosthesis for Calcific Aortic Stenosis: First Human Case Description," Circulation (2002) 3006-3008.

Davidson et al., "Percutaneous therapies for valvular heart disease," Cardiovascular Pathology 15 (2006) 123-129.

European Search Report issued in EP 10183557, mailed Apr. 11, 2011, 7 pages.

European Search Report issued in EP App No. 08165227, dated Mar. 13, 2009.

European Search Report issued in EP Application No. 05004289, dated Jun. 2, 2005, 3 pages.

European Search Report issued in EP Application No. 06101425, dated May 3, 2006, 6 pages.

European Search Report issued in EP Application No. 08150075, dated Mar. 27, 2008, 6 pages.

European Search Report issued in EP Publication No. 1570809 (EP App No. 05004289.4), dated Jan. 5, 2007, 5 pages.

Extended European Search Report issued in EP 09179414, dated Oct. 18, 2010, 8 pages.

Extended European Search Report issued in EP App No. 09158822, dated Sep. 29, 2009, 5 pages.

Hanzel, et al., "Complications of percutaneous aortic valve replacement: experience with the CriberEdwardsTm percutaneous heart valve," EuroIntervention Supplements (2006), I (Supplement A) A3-A8.

Huber, et al., "Do Valved Stents Compromise Coronary Flow?" Eur. J. Cardiothorac. Surg. 2004;25:754-759.

International Search Report issued in International Application No. PCT/I B2006/000967, published as WO2006/085225, mailed Jul. 6, 2006.

Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.

Khambadkone, et al, "Percutaneous Implantation of Pulmonary Valves," Expert Review of Cardiovascular Therapy (England), Nov. 2003, pp. 541-548.

Khambadkone, et al, "Percutaneous Pulmonary Valve Implantation: Early and Medium Term Results," Circulation 108 (17 Supplement), Oct. 28, 2003, p. 1V-375.

Khambadkone, et al, "Percutaneous Pulmonary Valve Implantation: Impact of Morphology on Case Selection," Circulation 108 (17 Supplement), Oct. 28, 2003, p. IV-642-IV-643.

Lutter, et al, "Percutaneous Aortic Valve Replacement: An Experimental Study. I. Studies on Implantation," The Journal of Thoracic and Cardiovascular Surgery, Apr. 2002, pp. 768-776.

Lutter, et al, "Percutaneous Valve Replacement: Current State and Future Prospects," Annals of Thoracic Surgery (Netherlands), Dec. 2004, pp. 2199-2206.

Ma, Ling, et al., "Double-crowned valved stents for off-pump mitral valve replacement," European Journal of Cardio Thoracic Surgery, 28:194-198, 2005.

Medtech Insight, "New Frontiers in Heart Valve Disease," vol. 7, No. 8 (2005).

Palacios, "Percutaneous Valve Replacement and Repair, Fiction or Reality?" Journal of American College of Cardiology, vol. 44, No. 8 (2004) pp. 1662-1663.

Pavcnik et al., "Aortic and venous valve for percutaneous insertion," Min. Invas. Ther. & Allied Techol. 2000, vol. 9, pas. 287-292.

Pelton et al., "Medical Uses of Nitinol," Materials Science Forum vols. 327-328, pp. 63-70 (2000).

Ruiz, "Transcathether Aortic Valve Implantation and Mitral Valve Repair: State of the Art," Pediatric Cardiology, vol. 26, No. 3 (2005).

Saliba, et al, "Treatment of Obstructions of Prosthetic Conduits by Percutaneous Implantation of Stents," Archives des Maldies du Coeur et des Vaisseaux (France), 1999, pp. 591-596.

Stassano et al., "Mid-term results of the valve-on-valve technique for bioprosthetic failure," Eur. J. Cardiothorac. Surg. 2000; 18:453-457.

Webb, et al., "Percutaneous Aortic Valve Implantation Retrograde from the Femoral Artery," Circulation (2006), 1 13;842-850.

* cited by examiner

MINIMALLY-INVASIVE CARDIAC-VALVE PROSTHESIS

CROSS REFERENCE TO RELATED APPLICATION

This application claims priority from Italian patent application number TO2004/A000135, filed on Mar. 3, 2004, which is hereby incorporated by reference.

TECHNICAL FIELD

The present invention relates to cardiac-valve prostheses. More specifically, the present invention is directed to a prosthesis that is amenable to minimally-invasive implantation.

BACKGROUND

Recently, there has been increasing consideration given to the possibility of using, as an alternative to traditional cardiac-valve prostheses, valves designed to be implanted using minimally-invasive surgical techniques or endovascular delivery (the so-called "percutaneous valves"). Implantation of a percutaneous valve (or implantation using thoracic-microsurgery techniques) is a far less invasive act than the surgical operation required for implanting traditional cardiac-valve prostheses. Further details of exemplary percutaneous implantation techniques are provided in U.S. Publication 2002/0042651, U.S. Pat. No. 3,671,979, and U.S. Pat. No. 5,954,766, which are hereby incorporated by reference.

These prosthetic valves typically include an anchoring structure, which is able to support and fix the valve prosthesis in the implantation position, and prosthetic valve elements, generally in the form of leaflets or flaps, which are stably connected to the anchoring structure and are able to regulate blood flow.

Furthermore, the methods of implantation of valves via a percutaneous route or by means of thoracic microsurgery are very frequently irrespective of the effective removal of the natural valve leaflets. Instead, the cardiac valve may be introduced in a position corresponding to the natural annulus and deployed in situ by simply divaricating definitively the natural valve leaflets.

There is a need for a percutaneous valve that does not run the risk of being displaced (dislodged) with respect to the implantation position, as a result of the hydraulic thrust exerted by the blood flow. There is a further need for a percutaneous valve that secures tightly to the flow duct generally defined by the natural valve annulus, such that it resists blood flow around the outside of the percutaneous valve structure.

SUMMARY

In an exemplary embodiment, the invention described herein is based on the concept of separating, in the framework of the supporting armature of the valve, the function of anchorage of the valve in the implantation site (including the possible function of sealing the valve with respect to the blood-flow duct natural to the region in which the valve is implanted) and the valve function proper. In a preferred way, this purpose is achieved by providing, within the armature of the valve, two structures (which are functionally distinct, but which in effect may be structurally integrated with one another), which are delegated separately to the accomplishment of these two functions. These two structures or portions comprise an external portion which can be spread out to enable anchorage of the cardiac-valve prosthesis at the implantation site, and an internal portion, which is substantially axially coextensive with the external portion, for supporting the prosthetic valve leaflets. The valve thus obtained is adapted in a particularly advantageous way to be implanted in a position corresponding to the so-called Valsalva's sinuses.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Figure 1:
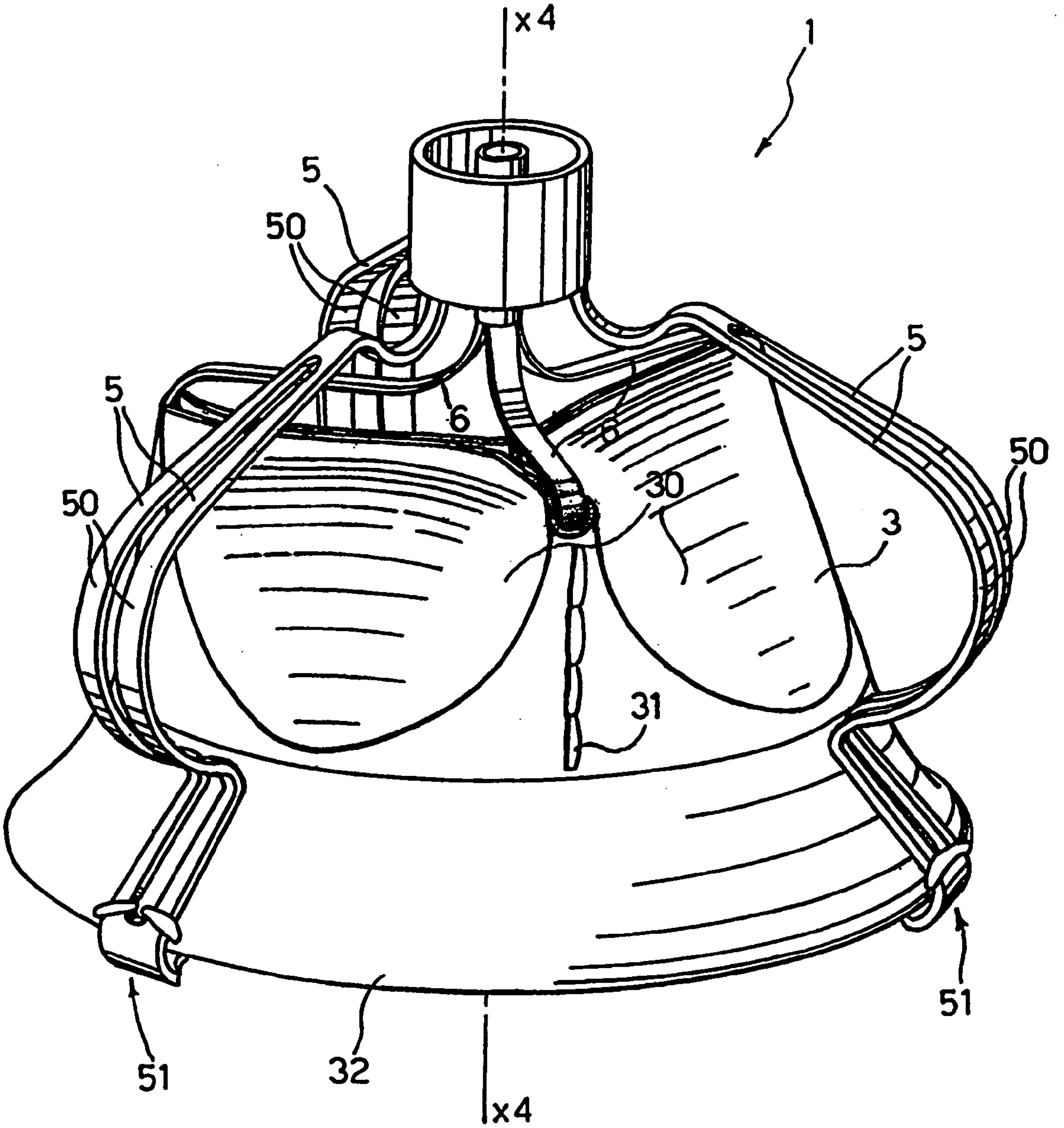
FIG. 1 is a general perspective view of a prosthetic valve according to the invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

In the figures, the reference number 1 designates as a whole a cardiac valve, which can be implanted via percutaneous route or resorting to thoracic-microsurgery techniques. These percutaneous implantation techniques are generally known in the art, and include those techniques described in the documents referenced above.

Figure 2:
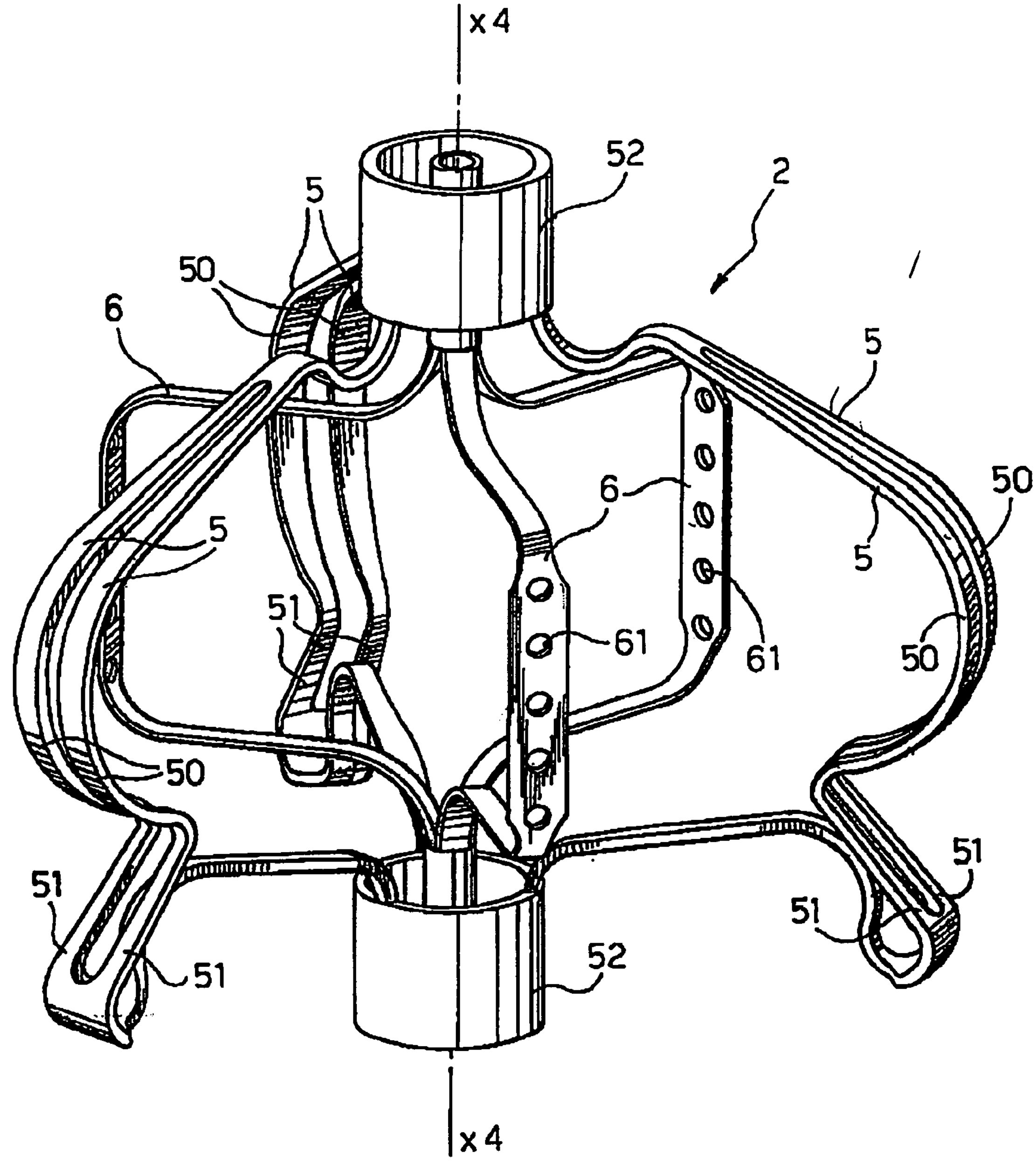
FIG. 2 illustrates the corresponding armature of the valve without the leaflets.

The valve 1 represented in FIGS. 1 and 2 is basically made up of two elements, namely an armature 2, having the characteristics that emerge more clearly from the representation of FIG. 2, and a set of leaflets 3, coupled to the armature 2. The characteristics of the leaflets 3 may be appreciated more fully from the view of FIG. 1.

As shown in FIG. 2, the armature 2 of the valve has a general cage-like structure comprising a set of ribs that extend with a general symmetry of a cylindrical type about a principal axis X4. In percutaneous valves, the axis X4 usually corresponds to the principal axis of the distal part of the catheter used for implantation of the valve 1. For the present purposes, the axis X4 can be viewed basically as an entity of a purely geometrical nature, even though it can in effect be identified either with elements of the implantation catheter or with elements of the armature 2 of the valve 1.

The armature 2 includes a distinguishable first and a second series of ribs designated, respectively, by the reference numbers 5 and 6. These ribs are usually made of metal material that is able to present characteristics of radial expandability, both as a result of a positive action of a dilatation or divarication force exerted by, for example, a balloon catheter and as a result of characteristics proper to the material constituting the ribs 5 (and possibly 6). In particular, the ribs may be made of a superelastic material and/or a material with shape-memory characteristics. A material that is well known in biomedical applications and that presents these characteristics is the material known as Nitinol.

Structures that may substantially be likened to cages, which can be introduced into a vessel of the human body and in particular into a venous site and can then be dilated in loco via dilatation of a distal part of the introducing catheter or, in the case of materials with shape-memory characteristics or the like, as a result of the retraction of a sheath that maintains the structure in a compressed position, are well known in the art. For example, these structures are well known in stent technology and, in particular, the technology of stents for angioplasty.

Due to the possibility of providing cage-like structures with ribs extending with a profile more or less shaped in diametral planes with reference to a principal axis, such as for example the axis X4, further reference may be made to technologies adopted for the fabrication of devices for the mapping or passivation of endocardial sites, such as, typically, endocavitary sites, used for localization and/or treatment of the so-called ectopic sites characteristic of the pathological conditions of a fibrillative type.

The distinction made between the ribs 5 and 6 is based on the fact that, within the armature 2, these different sets of ribs are designed to perform different functions, regardless of whether the ribs constitute physically distinct parts or are different portions of a unitary structure within the armature 2. In particular, the ribs 5 form an external part or anchor portion of the armature 2 designed (see FIG. 1) to enable the location and anchorage of the valve 1 at the implantation site. The ribs 6 are designed to constitute a more internal part or support portion of the armature 2, specifically the part that is to support the valve leaflets 30 of the prosthesis. Essentially, the ribs 5 and 6 are designed to define, within the armature 2, an external portion (ribs 5), which can be spread out or radially expanded to enable anchorage of the prosthesis 1 in the implantation site and an internal portion (ribs 6), which supports the prosthetic valve leaflets 30 provided in the set of leaflets 3.

An important characteristic of the solution described herein is provided by the fact that the two portions of the armature 2 are "substantially axially coextensive" with respect to one another. This definition is understood to indicate synthetically the fact that the two portions occupy, in the direction of the axis X4, axial stretches that are substantially coincident with one another. This is in direct contrast with solutions such as the one described, for example, in the U.S. Pat. No. 6,482,228, which illustrates a valve comprising two homologous portions that are totally staggered with respect to one another in an axial direction so that they can be located, one in a proximal position and the other in a distal position with respect to the coronary ostia.

The ribs 5, which in what follows are designated also as "external" ribs, are preferably arranged in sets of ribs, said sets being typically arranged in threes or multiples of three so as to be more readily adaptable, in a complementary way, to the anatomy of the Valsalva's sinuses, which is the site of choice for implantation of the valve 1.

In an exemplary embodiment, within the ribs 5 there is distinguishable a top part or top branch 50 and a bottom part or bottom branch 51. In the implantation position, the top parts or branches 50 are able, when they are in the deployed or expanded position, to extend within the so-called Valsalva's sinuses. The Valsalva's sinuses are the dilatations, from the overall lobed profile, which are present at the root of the aorta, hence in a physiologically distal position with respect to the aortic valve annulus. The bottom portions or branches 51 (see FIG. 1) are instead designed to extend in a proximal position with respect to the valve annulus so as to extend for a certain stretch within the ventricular chamber.

As a whole, the top parts 50 of the ribs 5, when brought into the extended position, jointly define a tripodal structure, which, by expanding within the Valsalva's sinuses, enables attainment of a condition of firm anchorage of the valve 1. This avoids the possibility of the valve 1, once implanted, being dislodged or even just displaced with respect to the implantation position, as a result of the hydraulic stresses applied thereto during operation by the blood flow.

The anchorage of the valve 1 in the implantation site is further reinforced by the fact that the area of radiusing between the top branches 50 and the bottom branches 51 of the ribs 5 has, precisely on account of the general divaricated or flared pattern of the bottom branches 51, an area of convexity that is thus positioned astride of the valve annulus, reinforcing the condition of shape fit between the armature of the valve and the implantation site. In the schematic representation of the figures, the natural valve leaflets of the valve that is to be replaced with the prosthetic valve 1 are not specifically illustrated.

The valve 1 described herein can be located in situ regardless of whether the natural valve leaflets have previously been removed or (and in a way that is from certain points of view preferred), without proceeding to the removal of said natural valve leaflets, by simply introducing the valve within the valve orifice and thus bringing about, as a result of the divarication of the valve 1 structure, the corresponding definitive divarication of the natural valve leaflets that are brought into, and maintained in, a position of substantial adherence to the surrounding portion of the valve annulus.

The particular conformation of the ribs 5, and in particular of the parts 50 and 51 just described, corresponds to the solution envisaged for the implantation of the valve 1 in the aortic site. Similar structures can be adopted for implantations, for example, in the mitral site.

The top and bottom branches 50 and 51 may in actual fact present conformations that are altogether different from the ones illustrated. For example, the top branches 50 may possibly present a conformation that is approximately symmetrical to the conformation represented herein with reference to the bottom branches 51, thus conferring on the external part of the armature of the valve 2 an overall hourglass conformation. Moreover, the presence of both of the branches 50 and 51 is altogether optional.

Again, in the exemplary embodiment illustrated herein, the terminal top ends of the branches 50 and the bottom ends of the branches 51 are connected to collar parts 52, which are designed to be fitted around, and usually to slide along the principal axis X4 during divarication of the armature 2. This solution proves advantageous as regards to the simplicity and the structural congruence of the armature 2. Recourse thereto should, however, be reconciled with the need to prevent the collar parts 52 from possibly ending up playing an excessive role of obstruction in regard to the blood flow that is to pass (from below upwards, with reference to the configuration of implantation as represented in FIG. 1) through the central orifice of the valve 1 defined between the valve leaflets 30 in a divaricated position. For example, it is conceivable to use just one of the collars 52, for example the one illustrated in the bottom portion in FIG. 2.

The structure and the configuration of the ribs 6 is, as a whole, akin to that of the ribs 5. In the case of the ribs 6, which form the internal part of the armature 2 of the valve 1, there is, however, usually the presence of just three elements that support, in a position corresponding to homologous lines of commissure (which take material form as sutures 31 passing through openings 61 provided on the elements 6), the valve leaflets 30. Essentially, the complex of ribs 6 and valve leaflets 30 is designed to form the normal structure of a biological valve prosthesis. This is a valve prosthesis which (in the form that is to be implanted with a surgical operation of a traditional type, hence of an invasive nature) has met with a wide popularity in the art.

The structural details of biological valve prostheses, consisting of a tubular structure made of biological material (for example, the pericardium or meningeal tissue of animal origin) subjected to treatments of passivation (with gluteraldehyde or similar compounds) or alternatively a biocompatible synthetic material, after prior possible shaping of the cusp-like areas that are to constitute the prosthetic valve leaflets 30, are well known in the art. For further details of the structure of such a valve, reference can be made to EP-B-0 155 245, which is hereby incorporated by reference. For further details of the technology of fabrication and/or treatment of the material of the prosthetic valve leaflets, useful reference can be made to EP-B-0 133 420, which is hereby incorporated by reference.

In addition to the more strictly "valve" part comprising the prosthetic valve leaflets 30 supported in a commissural position by the ribs 6 of the armature 2, the leaflet part of the prosthesis illustrated also has an apron-like part 32, which extends according to a general chimney-like or flared configuration and is supported by the bottom parts 51 of the external ribs 5 of the armature 2. For this purpose, the bottom parts 51 have an overall V-shaped structure, hence comprising two branches that are to enclose within them the chimney-like portion 32 of the set of leaflets 3 of the valve armature 2, so causing this to be divaricated at the moment of spreading out of the valve and maintained in said divaricated position in the intraventricular site in a proximal position with respect to the valve annulus.

Albeit conserving an extreme structural simplicity, from which there derives a corresponding reliability during implantation, the valve structure described manages to meet in an excellent way various needs that in themselves contrast with one another. This is obtained basically by separating the two parts of the armature 2, which are functionally distinct, even though they may be integrated in a single structure, and hence delegating to them two different functions.

In particular, the external ribs 5 (and more specifically when these are present in the two branches 50 and 51, which can be positioned astride of the valve annulus) provide the firm anchorage of the valve in situ, so preventing it from possibly being removed or even just displaced from the implantation site chosen by the person carrying out the implantation operation. This is obtained with a structure that is able to adapt to the natural anatomical conformation without exerting thereon stresses of a traumatic nature.

As shown in the Figures, the ribs 5 can present a rather thin or light structure. This allows them to adhere to the walls of the root of the aorta, to the surrounding portion of the valve annulus, and to the walls of the endocardial chamber, without exerting particularly marked stresses on those walls, which—in extreme cases—could even be at the basis of phenomena of lesions and, even more, of onset of reactions of the organism in regard to said lesions. The action of anchorage is in fact achieved, more than for any other reason, on account of the presence of numerous ribs 5 and their conformation, which is complementary with respect to that of the implantation site (in particular, when this is represented by the Valsalva's sinuses).

The internal part of the armature 2, represented by the ribs 6, enables, spreading out and support of the prosthetic valve leaflets 30 in the implantation position. This is achieved by recourse to a structure and a conformation which, precisely because they reproduce very closely those of traditional prosthetic valves of a biological type, prove particularly suitable and efficient for performing substitution of a defective natural valve. In particular, it is well known that valve prostheses of a biological type, precisely because they are able to reproduce closely the fluid-dynamic characteristics and the characteristics of behaviour of the leaflets of natural cardiac valves, can be used to benefit patients affected by forms of rather marked cardiac insufficiency. This possibility is achieved in an optimal way in the solution described herein precisely because the valve function is rendered altogether independent of the function of anchorage in situ of the prosthesis.

The presence of the branches 51 in the armature 2 of the prosthesis and, conversely, of the apron-like or chimney-like portion 32 in the set of leaflets 3 (in addition to contributing further to the shape fit and hence to the anchorage in the implantation site of the valve 1) likewise enables very efficient channelling of the blood flow coming from the heart, channelling it in a practically complete way, precisely on account of the divaricated or flared configuration of the chimney-like portion 32 within the flow duct defined within the valve leaflets 30. There is thus minimized (and in effect cancelled out) shortly following implantation, the possibility of there being created lines of blood flow that pass on the outside of the cardiac-valve prosthesis.

The foregoing likewise envisages that the two parts or portions of armature 2 are substantially axially coextensive with respect to one another, occupying, if viewed in their development in the direction of the axis X4, axial stretches substantially coinciding with one another. This characteristic enables a precise positioning of the prosthetic valve leaflets in a "physiological" location (i.e., in a location basically corresponding to the location of the natural valve leaflets), likewise benefiting, for the purposes of the anchorage of the prosthesis in situ, from a shape fit with the Valsalva's sinuses.

Figure 3:
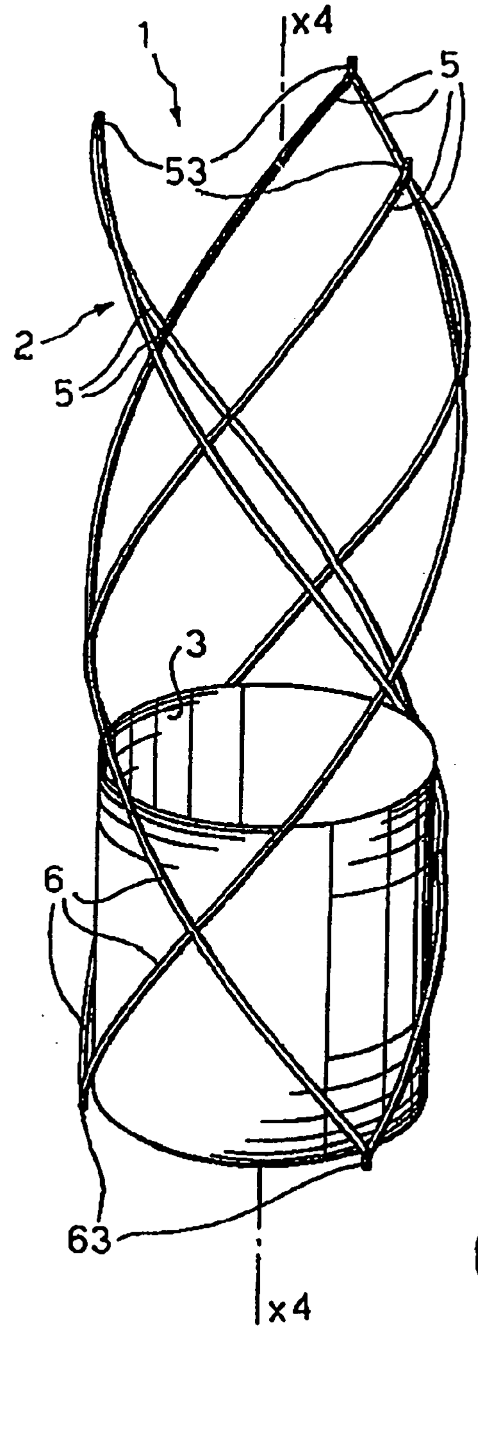
FIGS. 3 and 4 illustrate a second exemplary embodiment of a prosthetic valve according to the invention.
Figure 4:
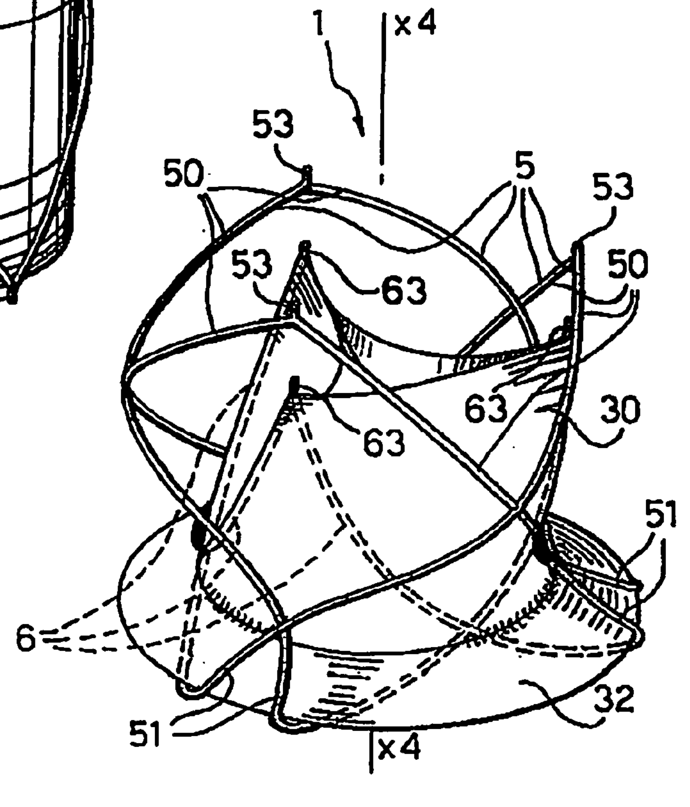

FIGS. 3 and 4 illustrate a second exemplary embodiment of a cardiac valve, according to the present invention. From a general structural standpoint, the valve of FIGS. 3 and 4 derives basically from the structure of the valve shown in FIGS. 1 and 2. The valve according to FIGS. 3 and 4 is obtained by recourse, as regards the armature, to a single element of tubular shape and reticular structure. In particular, FIG. 3 illustrates this tubular element in an "extroverted" or "extended" configuration, whereas in FIG. 4 the same element is illustrated in an "introverted" configuration, corresponding to the final conformation of implantation of the valve.

In this particular embodiment, the two parts or portions of the armature 2 (the external portion 5 for anchorage of the valve 1 in the implantation site and the internal portion 6 with the function of supporting the valve leaflets) are integrated in a single structure consisting precisely of the tubular element referred to previously. This element, designated as a whole by reference numeral 2, has a substantially cylindrical structure that develops about a principal axis X4 and consists of ribs having a general helical conformation and presenting joints in pairs 53 and 63 at the two ends. The armature 2 is without any discontinuity between the external portion 5 and the internal portion 6 of the ribs. The ribs that form the armature 2 in this embodiment are basically made of a superelastic material and/or shape-memory material.

The valve 1 passes from the extroverted configuration (FIG. 3) to the introverted or final configuration (FIG. 4) through a mechanism of deformation that may be obtained at the implantation site. This can occur, in the case of percutaneous valves, via remote manipulation devices associated to the catheter for introduction of the valve. Said devices are in themselves known in so far as they are used in association with catheters of various types, for example to obtain actions of selective spreading out of implantation devices, such as stents, stent-grafts or the like.

The mechanism of deployment (i.e., introversion) in question involves passing from the extended conformation of FIG. 3 to the final conformation of FIG. 4, thereby causing the joints 63, to which the set of leaflets 3 are fixed (internally with respect to the original cylindrical tubular element), to converge within the tubular structure and then advance therein until the joints 63 arrive in the proximity of the joints 53, which, at the start of the movement of introversion described, were exactly at the opposite end of the original cylindrical tubular element.

Basically, this movement causes the tubular element 2 to pass between an extroverted configuration (FIG. 3), in which said tubular element has a substantially cylindrical shape, with the external portion 5 and internal portion 6 of the armature axially juxtaposed with respect to one another, and a final introverted configuration (FIG. 4), in which the external portion 5 and internal portion 6 are substantially axially coextensive with respect to one another.

This overall movement is usually accompanied by at least a slight divarication of the joints 53 and of the areas of the armature of the valve (external part 5) adjacent thereto. This divarication of the joints 53 and of the areas of the armature adjacent thereto is clearly perceptible in FIG. 4. In the same figure there is moreover perceptible the action of “pinching” of the apron-like part of the leaflet, which may be achieved with a positive action of deformation of the armature and/or by exploiting the shape-memory characteristics of the constituent material. Also in this case, a final configuration is reached, in which the external portion 5 and internal portion 6 of the armature 2 of the valve 1 are substantially axially coextensive with respect to one another, finding themselves occupying axial stretches that substantially coincide with respect to the axis X4.

In the introverted configuration (see FIG. 4), it is possible to distinguish top branches 50 and bottom branches 51 of the ribs 5, in a conformation suitable for being implanted in the Valsalva’s sinuses. The top branches 50 extend in a generally cage-like form, which is complementary with the lobed anatomy of the Valsalva’s sinuses and co-operate with the bottom branches 51, which are to extend in a proximal position with respect to the valve annulus so as to be introduced within the ventricular chamber, ensuring a firm anchorage of the valve 1 at the implantation site. The set of leaflets 3 comprises the prosthetic valve leaflets 30 supported by the internal ribs 6 and an apron-like part 32 supported by and fixed to the bottom branches 51 of the external ribs 5.

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

We claim:

1. A cardiac-valve prosthesis adapted for percutaneous implantation, the prosthesis comprising:

an armature adapted for deployment in a radially expanded implantation position, the armature including a support portion and an anchor portion, which are substantially axially coextensive with respect to one another, the anchor portion and the support portion adapted to assume independent radially expanded configurations when the armature is in the radially expanded implantation position; and a plurality of leaflets coupled to the support portion, which can be deployed with the armature in the implantation position, wherein the leaflets define, in the implantation position, a flow duct;

wherein the anchor portion can be deployed to enable anchorage of the cardiac-valve prosthesis at an implantation site.

2. The prosthesis according to claim 1 wherein the anchor portion and the support portion of the armature are structurally distinct from one another.

3. The prosthesis according to claim 2 wherein the anchor portion of the armature has a set of ribs which, in the implantation position, are adapted to conform to a shape of the implantation site.

4. The prosthesis according to claim 3 wherein the ribs have at least one arched portion having an overall arched pattern.

5. The prosthesis according to claim 4 wherein the ribs of the anchor portion of the armature have a plurality of branches adapted to extend in an endocardial position.

6. The prosthesis according to claim 5 wherein the ribs of the anchor portion of the armature have a convex portion that is adapted to position astride a valve annulus site.

7. The prosthesis according to claim 5 wherein the ribs of the anchor portion of the armature include, respectively, a first branch and a second branch adapted to extend, respectively, in a distal position and a proximal position with respect to a valve annulus site.

8. The prosthesis according to claim 5 wherein the ribs of the anchor portion of the armature are grouped together into three sets, the sets being spaced generally equidistant about a circumference of the armature.

9. The prosthesis according to claim 1 wherein the support portion of the armature includes support ribs that are able to support the prosthetic valve leaflets in a commissural position.

10. The prosthesis according to claim 9 wherein the support ribs are grouped together into three sets.

11. The prosthesis according to claim 1 wherein the armature is obtained from a tubular element comprising ribs having a general helical conformation.

12. The prosthesis according to claim 11 wherein the ribs are made of a superelastic material or a shape-memory material.

13. A cardiac-valve prosthesis adapted for percutaneous delivery and implantation at an anatomical valve site having a Valsalva sinus, the prosthesis comprising:

an armature adapted for delivery in a radially-compressed configuration and deployment in a radially-expanded configuration at the valve site, the armature including a support portion and an anchor portion; and a plurality of leaflets coupled to the support portion, which can be deployed with the armature in the radially-expanded configuration, wherein the leaflets define a flow duct;

wherein the anchor portion includes ribs that in the radially-expanded configuration generally conform to the Valsalva sinus to enable anchorage of the cardiac-valve prosthesis at the valve site.

14. The prosthesis according to claim 13 wherein the anchor portion and the support portion of the armature are structurally distinct from one another.

15. The prosthesis according to claim 14 wherein the ribs include a proximal portion generally shaped to conform to an intraventricular portion of the valve annulus.

16. The prosthesis according to claim 14 wherein the anchor portion includes three sets of ribs, the ribs spaced circumferentially about the armature such that each set of ribs is adapted to generally conform to each or three corresponding Valsalva sinuses.

17. The prosthesis according to claim 13 wherein the ribs are made from Nitinol.

18. The prosthesis according to claim 17 wherein the ribs are shaped to generally conform to the Valsalva sinus.

19. The prosthesis according to claim 18 wherein the ribs are shaped to apply a non-traumatic amount of stress to the Valsalva sinus.

20. The prosthesis according to claim 13 wherein the ribs of the anchor portion of the armature have a convex portion that, in a pre-stressed condition, is shaped to position astride a valve annulus site.

21. A cardiac valve prosthesis comprising:

an armature adapted to anchor the prosthesis at an implantation site generally corresponding to a location of a natural cardiac valve;

a plurality of prosthetic valve leaflets coupled to the armature and defining a flow duct; and an apron-like portion coupled to the prosthetic valve leaflets, the apron-like portion being shaped to extend radially outward with respect to the flow duct and configured to substantially prevent flow outside the flow duct when the prosthesis is anchored at the implantation site.

22. The prosthesis of claim 21 wherein the apron-like portion is adapted to channel flow through the flow duct when the prosthesis is anchored at the implantation site.

23. The prosthesis of claim 21 wherein the natural cardiac valve includes an annulus, and the apron-like portion is adapted to be positioned proximal to the annulus and to substantially prevent flow outside the flow duct when so positioned.

24. The prosthesis of claim 23 wherein the natural cardiac valve is the aortic valve and further wherein the apron-like portion is configured to be positioned proximal to the annulus and to extend radially from the annulus within the ventricular chamber.

25. The prosthesis of claim 21 wherein the armature includes a plurality of ribs each including branched portions shaped to support the apron-like portion.

26. A cardiac valve prosthesis adapted for anchorage at an implantation site generally corresponding to a natural cardiac valve having an annulus, the prosthesis comprising a valve portion defining a flow duct, and an apron-like portion adapted to be positioned proximal to the annulus and to substantially prevent flow outside the flow duct when the prosthesis is anchored at the implantation site.

27. The prosthesis of claim 26 wherein the apron-like portion is adapted to flare radially outward with respect to the flow duct and to channel flow through the flow duct when the prosthesis is anchored at the implantation site.

28. The prosthesis of claim 26 wherein the natural cardiac valve is the aortic valve and further wherein the apron-like portion is configured to be positioned proximal to the annulus and to extend radially from the annulus within the ventricular chamber.

* * * * *